United States Patent
Konno et al.

(10) Patent No.: US 9,901,267 B2
(45) Date of Patent: Feb. 27, 2018

(54) CARDIONPULMONARY FUNCTION EVALUATING APPARATUS AND CARDIONPULMONARY FUNCTION EVALUATING METHOD

(71) Applicant: NIHON KOHDEN CORPORATION, Tokyo (JP)

(72) Inventors: Norihito Konno, Tokyo (JP); Makoto Hajiri, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 61 days.

(21) Appl. No.: 14/638,612

(22) Filed: Mar. 4, 2015

(65) Prior Publication Data

US 2015/0257656 A1    Sep. 17, 2015

(30) Foreign Application Priority Data

Mar. 14, 2014    (JP) .................................. 2014-051095

(51) Int. Cl.
*A61B 5/029*    (2006.01)
*A61B 5/0402*    (2006.01)
(Continued)

(52) U.S. Cl.
CPC ............ *A61B 5/029* (2013.01); *A61B 5/0245* (2013.01); *A61B 5/02416* (2013.01);
(Continued)

(58) Field of Classification Search
CPC .. G06F 19/3431–19/3443; G06F 19/26; G06F 19/3406; A61B 5/029; A61B 5/0295; A61B 5/7271–5/7282; A61B 5/02028
See application file for complete search history.

(56) References Cited

U.S. PATENT DOCUMENTS

2003/0167012 A1    9/2003    Friedman et al.
2005/0222514 A1    10/2005    Sugo et al.
(Continued)

FOREIGN PATENT DOCUMENTS

EP    2 241 251 A1    10/2010
JP    2005-312947 A    11/2005
(Continued)

OTHER PUBLICATIONS

The extended European search report for the related European Patent Application No. 15157685.7 dated Jul. 21, 2015.
(Continued)

*Primary Examiner* — Michael Kahelin
(74) *Attorney, Agent, or Firm* — Pearne & Gordon LLP (57) ABSTRACT

A cardiopulmonary function evaluating apparatus includes: an electrocardiogram measuring unit which is configured to measure an electrocardiogram of a subject; a photoplethysmogram detecting unit which is configured to detect a photoplethysmogram of the subject; a heart rate calculating unit which is configured to calculate a heart rate (HR) of the subject based on the electrocardiogram; a PWTT calculating unit which is configured to calculate a pulse wave transmission time (PWTT) of the subject based on the electrocardiogram and the photoplethysmogram; an SV calculating unit which is configured to calculate a stroke volume (SV) of the subject based on the heart rate and the pulse wave transmission time; and an outputting unit which is configured to output a state related to the stroke volume of the subject based on the stroke volume that is calculated by the SV calculating unit.

12 Claims, 8 Drawing Sheets

(51) Int. Cl.
    *A61B 5/0245*    (2006.01)
    *A61B 5/024*     (2006.01)
    *A61B 5/00*      (2006.01)
    *A61B 5/0452*    (2006.01)
    *A61B 5/0285*    (2006.01)

(52) U.S. Cl.
    CPC .......... *A61B 5/0402* (2013.01); *A61B 5/0452* (2013.01); *A61B 5/7278* (2013.01); *A61B 5/0285* (2013.01)

(56)    References Cited

U.S. PATENT DOCUMENTS

| 2007/0021678 | A1* | 1/2007 | Beck .................... | A61B 5/0245 |
|  |  |  |  | 600/510 |
| 2008/0183232 | A1* | 7/2008 | Voss ................... | A61B 5/02028 |
|  |  |  |  | 607/24 |
| 2014/0249443 | A1* | 9/2014 | Banet ...................... | A61B 5/01 |
|  |  |  |  | 600/526 |
| 2015/0126820 | A1 | 5/2015 | Muhlsteff |  |

FOREIGN PATENT DOCUMENTS

| JP | 2007-44352 A | 2/2007 |
| WO | 2013/003787 A2 | 1/2013 |
| WO | 2013-171599 A1 | 11/2013 |

OTHER PUBLICATIONS

Japanese Office action issued in Patent Application No. JP 2014-051095 dated Apr. 3, 2017.

* cited by examiner

| ATTRIBUTE / AGE | MALE ATHLETE (YELLOW RACE) | MALE ATHLETE (BLACK RACE) | ORDINARY MALE (YELLOW RACE) | ORDINARY MALE (BLACK RACE) |
|---|---|---|---|---|
| 16 - 20 | XXX1 | XXX2 | XXX3 | XXX4 |
| 21 - 25 | XXX5 | XXX6 | XXX7 | XXX8 |
| — | — | — | — | — |

FIG. 8

CARDIONPULMONARY FUNCTION EVALUATING APPARATUS AND CARDIONPULMONARY FUNCTION EVALUATING METHOD

CROSS-REFERENCE TO RELATED APPLICATION(S)

This application is based upon and claims the benefit of priority from prior Japanese patent application No. 2014-051095, filed on Mar. 14, 2014, the entire contents of which are incorporated herein by reference.

BACKGROUND

The presently disclosed subject matter relates to a cardiopulmonary function evaluating apparatus and cardiopulmonary function evaluating method in which the cardiopulmonary function is evaluated by using an apparatus for measuring the volume of blood ejected with each beat of the heart.

As training for improving the cardiopulmonary function, altitude training and exercise under hypoxic conditions are performed. Usually, it is determined whether a sufficient effect is achieved in such training or not, based on a comparison before and after the training (for example, comparison between the measurement time of long-distance running conducted before the training, and that of long-distance running conducted after some time of the training), or a feeling of weariness. However, evaluation based on such a determination is not objective, and hence it is impossible to correctly acquire the effect of the training.

Patent Literature 1 discloses a technique related to a measurement index for improving the ability of the cardiopulmonary function. The cardiovascular function measuring apparatus for an athlete disclosed in Patent Literature 1 enables an athlete or the like to evaluate the comprehensive cardiovascular functions before, during, and after exercise. In the cardiovascular function measuring apparatus for an athlete, the heart rate (HR) and stroke volume (SV) of the subject are measured by using a technique in which the cardiac output is measured noninvasively and continuously for a long term (for details, see Patent Literature 2). In the cardiovascular function measuring apparatus for an athlete, then, a locus curve of the stroke volume (SV) which is measured in a process of increasing the heart rate (HR), and that of the stroke volume (SV) which is measured in a process of decreasing the heart rate (HR) are displayed on a same display unit. Thereafter, the cardiovascular function measuring apparatus for an athlete displays an evaluation of the cardiovascular function of the subject, based on the size of the area enclosed by the two locus curves. Here, the locus curves mean curves in a coordinate system in which the abscissa represents the heart rate (HR) and the ordinate represents a change of the stroke volume (SV).
(Patent Literature 1) JP-A-2007-44352
(Patent Literature 2) JP-A-2005-312947
(Non-Patent Literature 1) (Searched on Feb. 13, 2014), Internet, Nihon Kohden PWTT Principles
(Non-Patent Literature 2) Sakurai, Watanabe, "ME Hayawakari Q&A 3 Ketsuatsukei•Shinpakushutsuryokei•Ketsuryukei," Nankodo, p. 125-127

In order to improve the cardiopulmonary ability, it is important to increase the maximum oxygen consumption. The maximum oxygen consumption is expected to be improved by increasing the stroke volume (SV). When the condition of the stroke volume (SV) (for example, relationship between the number of elapsed days in the case where training is carried out every day, and a change of the stroke volume (SV)) is known, therefore, it is possible to know the exercise effect of the subject, and the state of the cardiopulmonary function of the subject while being compared with the states of other persons.

In the cardiovascular function measuring apparatus for an athlete disclosed in Patent Literature 1, the cardiopulmonary function of the subject is evaluated by the area enclosed by the two locus curves. The area is an area in a chart in which the abscissa represents the heart rate (HR) and the ordinate represents the stroke volume (SV), and therefore indicates a value related to the cardiac output (CO). From the area, the volume of blood which is pumped from the heart in a unit of time can be known, but it is impossible to know whether the area is obtained as a result depending on the stroke volume (SV) or that depending on the heart rate (HR). In other words, the cardiovascular function measuring apparatus for an athlete evaluates the cardiovascular function by using the cardiac output (CO). In the technique, therefore, the condition of the stroke volume (SV) itself such as the amount of change of the stroke volume (SV) cannot be adequately known.

SUMMARY

The presently disclosed subject matter may provide a cardiopulmonary function evaluating apparatus and cardiopulmonary function evaluating method in which the state of the cardiopulmonary function of the subject (for example, the degree of improvement in cardiopulmonary function, and comparisons with cardiopulmonary functions of the same generation) can be adequately known by using the stroke volume (SV).

The cardiopulmonary function evaluating apparatus may comprise: an electrocardiogram measuring unit which is configured to measure an electrocardiogram of a subject; a photoplethysmogram detecting unit which is configured to detect a photoplethysmogram of the subject; a heart rate calculating unit which is configured to calculate a heart rate (HR) of the subject based on the electrocardiogram; a PWTT calculating unit which is configured to calculate a pulse wave transmission time (PWTT) of the subject based on the electrocardiogram and the photoplethysmogram; an SV calculating unit which is configured to calculate an stroke volume (SV) of the subject based on the heart rate (HR) and the pulse wave transmission time (PWTT); and an outputting unit which is configured to output a state related to the stroke volume (SV) of the subject based on the stroke volume (SV) that is calculated by the SV calculating unit.

The outputting unit may output a temporal change of the stroke volume (SV) that is calculated by the SV calculating unit.

The outputting unit may output the temporal change of the stroke volume (SV) that is calculated by the SV calculating unit, in a form of a graph.

The outputting unit may display a temporal change of the stroke volume (SV) which is acquired by the SV calculating unit in one exercise, on the graph.

The SV calculating unit may acquire a plurality of temporal changes of the stroke volume (SV) in one exercise, and the outputting unit may superimposedly display a plurality of graphs based on the plurality of temporal changes of the stroke volumes (SV) which are acquired by the SV calculating unit.

The cardiopulmonary function evaluating apparatus may further comprise: an SV evaluating unit which is configured to evaluate a cardiopulmonary ability of the subject, based on the stroke volume (SV) calculated by the SV calculating unit and an index value related to the stroke volume (SV). The outputting unit may output a result of the evaluation by the SV evaluating unit, as the state related to the stroke volume (SV) of the subject.

The index value may include at least one of a history value of a stroke volume (SV) calculated by the SV calculating unit, and a statistical value of stroke volumes (SV) related to the subject.

The SV evaluating unit may calculate a difference (ΔesSV) between a current stroke volume (SV) which is calculated by the SV calculating unit, and the history value which is acquired at a predetermined timing.

The SV evaluating unit may refer to the history value, and calculate an amount of change (d(esSV)/dt) of the current stroke volume (SV) calculated by the SV calculating unit.

The SV evaluating unit may compare and evaluate the statistical value and the current stroke volume (SV) calculated by the SV calculating unit.

The cardiopulmonary function evaluating method may comprise: measuring an electrocardiogram of a subject; detecting a photoplethysmogram of the subject; calculating a heart rate (HR) of the subject based on the electrocardiogram; calculating a pulse wave transmission time (PWTT) of the subject based on the electrocardiogram and the photoplethysmogram; calculating an stroke volume (SV) of the subject based on the heart rate (HR) and the pulse wave transmission time (PWTT); and outputting a state related to the stroke volume (SV) of the subject based on the calculated stroke volume (SV).

The cardiopulmonary function evaluating apparatus may comprise: a noninvasive SV calculating unit which is configured to calculate a stroke volume (SV) of a subject by using a noninvasive technique; and an outputting unit which is configured to output a state related to the stroke volume (SV) of the subject based on the stroke volume (SV) that is calculated by the noninvasive SV calculating unit.

DETAILED DESCRIPTION OF EXEMPLARY EMBODIMENTS

Embodiment 1

Hereinafter, embodiments of the presently disclosed subject matter will be described with reference to the drawings.

Figure 1:
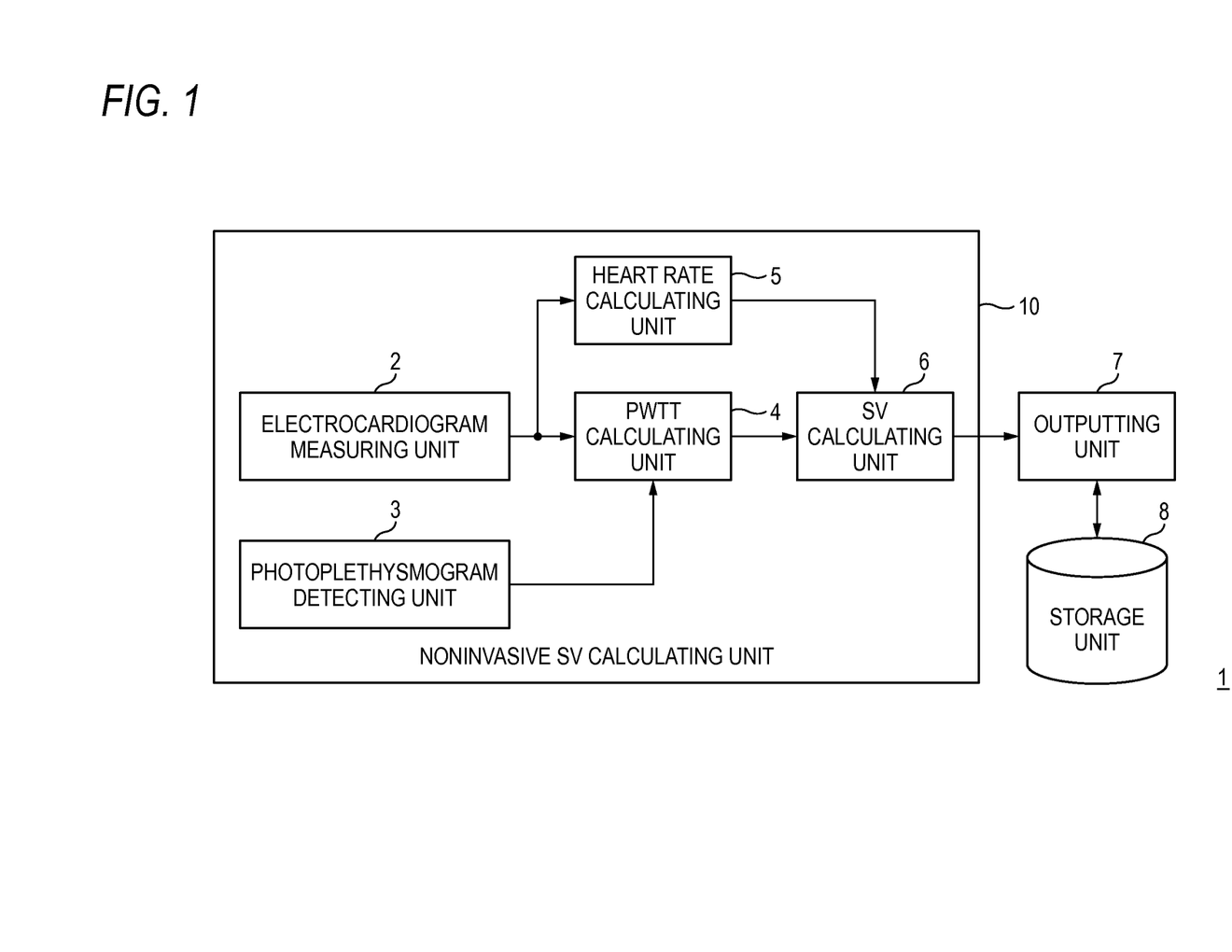
FIG. 1 is a block diagram showing the configuration of a cardiopulmonary function evaluating apparatus 1 of Embodiment 1.

FIG. 1 is a block diagram showing the configuration of a cardiopulmonary function evaluating apparatus 1 of the embodiment. The cardiopulmonary function evaluating apparatus 1 includes a noninvasive SV calculating unit 10, an outputting unit 7, and a storage unit 8. The noninvasive SV calculating unit 10 includes an electrocardiogram measuring unit 2, a photoplethysmogram detecting unit 3, a PWTT calculating unit 4, a heart rate calculating unit 5, and an SV calculating unit 6. The noninvasive SV calculating unit 10 calculates the stroke volume (SV) of the subject by using a noninvasive technique.

The electrocardiogram measuring unit 2 is connected to electrocardiogram electrodes which are not shown. The electrocardiogram electrodes are attached to the chest portion of the subject. The electrocardiogram measuring unit 2 acquires an electrocardiogram (ECG) based on electrocardiogram signals obtained from the electrocardiogram electrodes, and supplies the acquired electrocardiogram (ECG) to the PWTT calculating unit 4 and the heart rate calculating unit 5.

The photoplethysmogram detecting unit 3 is attached to a peripheral portion of the subject (for example, the finger of the subject). The photoplethysmogram detecting unit 3 performs usual SpO2 measurement or the like, and calculates the photoplethysmogram waveform of the subject. The photoplethysmogram detecting unit 3 supplies the calculated photoplethysmogram waveform of the subject to the PWTT calculating unit 4.

The heart rate calculating unit 5 calculates the heart rate (HR) based on the waveform of the electrocardiogram (ECG) measured by the electrocardiogram measuring unit 2. The heart rate calculating unit 5 supplies the calculated heart rate (HR) to the SV calculating unit 6.

The PWTT calculating unit 4 calculates the pulse wave transmission time (PWTT) based on the photoplethysmogram waveform and the electrocardiogram (ECG). As to relationship among the photoplethysmogram waveform, the electrocardiogram (ECG), and the pulse wave transmission time (PWTT), refer, for example, to Non-Patent Literature 1. The details of the method of calculating the PWTT may be similar to FIG. 2 of Patent Literature 1. The PWTT calculating unit 4 supplies the calculated pulse wave transmission time (PWTT) to the SV calculating unit 6.

The SV calculating unit 6 calculates the stroke volume (SV) based on the pulse wave transmission time (PWTT) and the heart rate (HR). The process of calculating the stroke volume (SV) in the SV calculating unit 6 is approximately identical with the flow shown in FIG. 2 of Patent Literature 1. The SV calculating unit 6 supplies the calculated stroke volume (SV) to the outputting unit 7.

The outputting unit 7 outputs a state related to the stroke volume (SV) of the subject based on the stroke volume (SV) which is calculated by the SV calculating unit 6. Here, the state related to the stroke volume (SV) means a concept including the temporal change of the value of the stroke volume (SV), evaluation values calculated from the value of the stroke volume (SV) (ΔesSV and (d(esSV)/dt) which will be described in Embodiment 2, and the like), a value of comparison between the value of the calculated stroke volume (SV) and a statistical value (for example, the average value of stroke volumes (SV) of persons of the same age as the subject, and the value will be described in detail in Embodiment 2), and the like. Preferably, the outputting unit 7 is processing means which is executed as programs by a CPU (Central Processing Unit, not shown in FIG. 1) incorporated in the cardiopulmonary function evaluating apparatus 1.

The storage unit 8 properly stores the stroke volume (SV) calculated by the SV calculating unit 6. Here, the storage unit 8 may be a storage unit which is disposed in the cardiopulmonary function evaluating apparatus 1, such as a hard disk drive, that which is detachable from the cardiopulmonary function evaluating apparatus 1, such as a USB (Universal Serial Bus) memory or a flash memory, or that which is disposed in a server communicable with the cardiopulmonary function evaluating apparatus 1.

Although the noninvasive SV calculating unit 10 in the above-described example calculates the stroke volume (SV) of the subject by using the electrocardiogram (ECG), the pulse wave transmission time (PWTT), and the heart rate (HR), the calculation method is not limited to this. The noninvasive SV calculating unit 10 may calculate the stroke volume (SV) of the subject by using another noninvasive method. For example, the noninvasive SV calculating unit 10 may calculate the stroke volume (SV) of the subject by using so-called impedance cardiography. Hereinafter, an example in which the stroke volume (SV) is calculated by using impedance cardiography will be described.

Two electrodes are attached around the neck or the like of the subject, and other two electrodes are attached around the chest or the like. A high-frequency power supply is connected to one of the electrodes on the side of the neck (the electrode is referred to as the electrode 1), and one of the electrodes on the side of the chest (the electrode is referred to as the electrode 4). Thereafter, a weak high-frequency current the degree of which does not affect the subject is supplied to the four electrodes (electrodes 1 to 4). As a result, a voltage the level of which is proportional to the impedance of the subject between the other electrode (electrode 2) on the side of the neck and the other electrode (electrode 3) on the side of the chest. Here, the noninvasive SV calculating unit 10 detects the voltage between the electrodes 2 and 3, and divides the voltage by the current value to calculate the impedance. The noninvasive SV calculating unit 10 substitutes the calculated impedance, the distance between the electrodes 2 and 3, and the blood resistance into the Kubicek equation, thereby calculating the stroke volume (SV) of the subject. For example, the details of impedance cardiography are described in Non-Patent Literature 2.

Hereinafter, a specific example of the outputting process of the outputting unit 7 will be described. More particularly, an example in which the outputting unit 7 outputs the temporal change of the stroke volume (SV) in the form of a graph will be described with reference to FIGS. 2 to 4.

Figure 2:
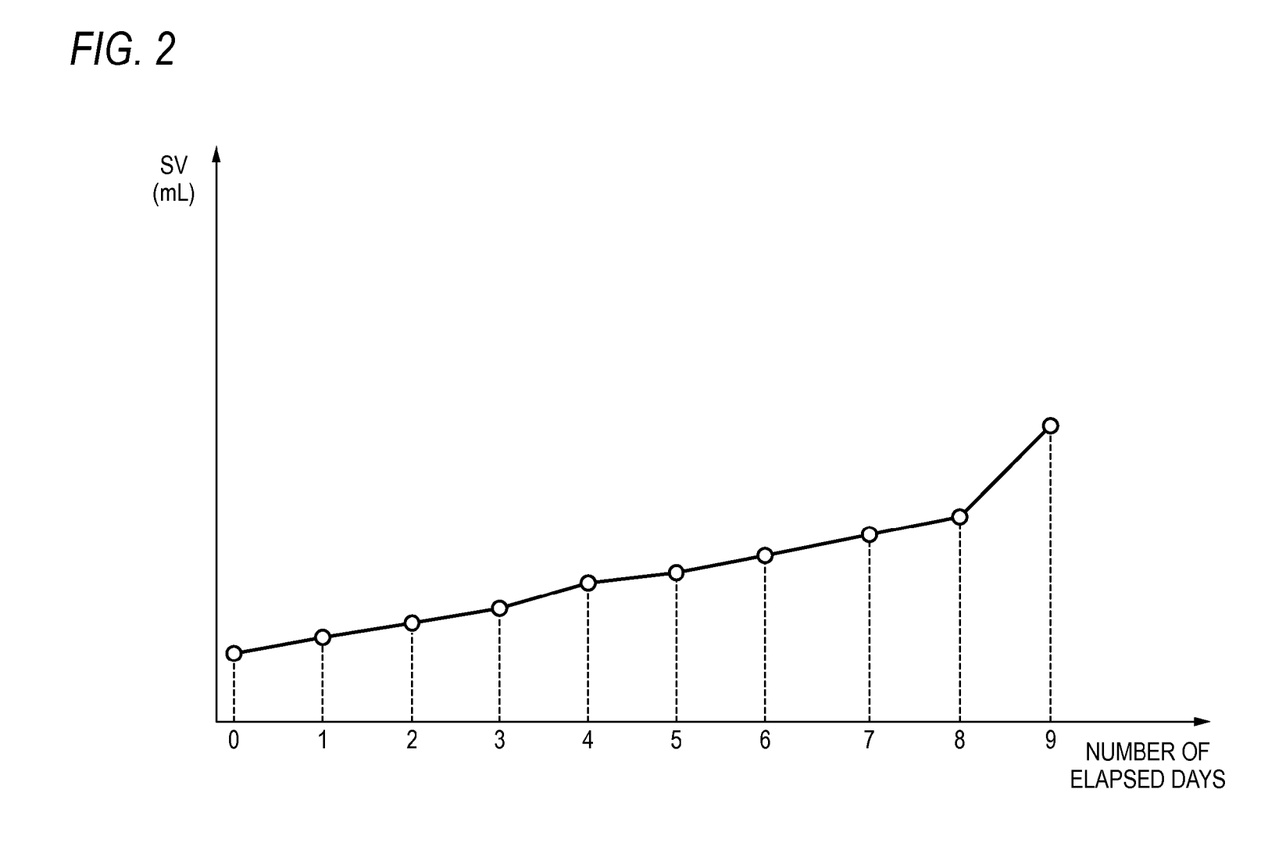
FIG. 2 is a conceptual view showing a first output example of an outputting unit 7 in Embodiment 1.

FIG. 2 is a conceptual view showing a first output example of the outputting unit 7. The following description is made assuming that, during when the subject continuously conducts training of long-distance running (for example, for one hour every day), the stroke volume (SV) is measured at a predetermined timing (for example, after the elapse of 45 minutes from the start of the running). Referring to FIG. 2, the outputting unit 7 outputs a graph showing the number of elapsed days of the training, and a change of the stroke volume (SV), to a displaying unit (for example, a displaying device integrated with the cardiopulmonary function evaluating apparatus 1).

When referring to the graph of FIG. 2, the subject (or another user such as a sport coach teaching the subject) can know the temporal change of the stroke volume (SV). In the example of FIG. 2, the present (ninth day) value of the stroke volume (SV) is improved as compared to the value at the timing (zeroth day) of starting training, and therefore the subject or the like can visually recognize that the cardiopulmonary function is improved by the training. The increasing rate from the value of the stroke volume in the eighth day to that of the stroke volume (SV) in the ninth day is large. Therefore, the subject can visually know that training of the ninth day is effective in improving the cardiopulmonary function.

Although, in the example of FIG. 2, the relationship between the number of elapsed days and the stroke volume (SV) are illustrated, the output manner is not limited to this. In the case where the subject conducts training two times per day (training in the forenoon, and that in the afternoon), the outputting unit 7 may plot the value on the graph twice per day.

Figure 3:
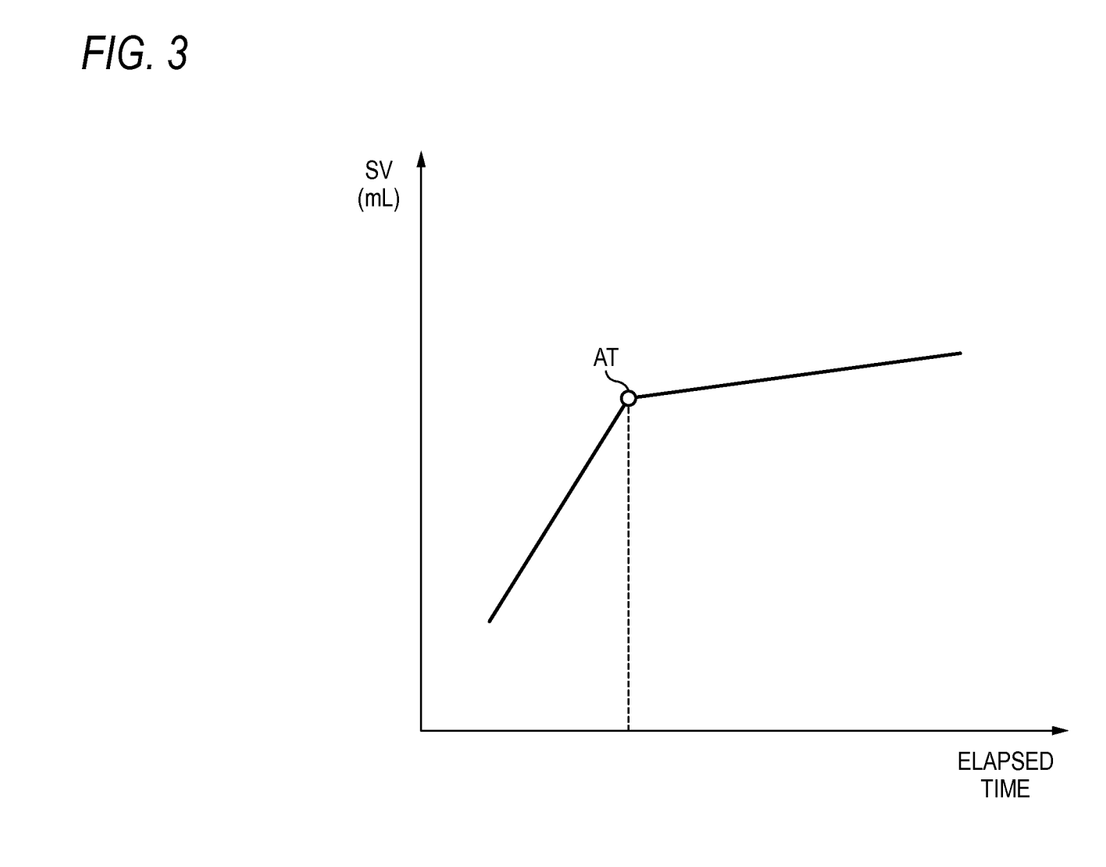
FIG. 3 is a conceptual view showing a second output example of the outputting unit 7 in Embodiment 1.

Then, a second output example of the outputting unit 7 will be described with reference to FIG. 3. FIG. 3 shows the relationship between the stroke volume (SV) in one exercise (for example, long-distance running for one hour, and, in other words, indicating one set of training), and the elapsed time. The SV calculating unit 6 continuously calculates the stroke volume (SV) in one exercise. The outputting unit 7 causes the temporal change of the stroke volume (SV) in one exercise which is calculated by the SV calculating unit 6, to be displayed in real time on the displaying unit as shown in FIG. 3.

In the case where exercise with load is continuously performed, the stroke volume (SV) is rapidly increased, and, after exceeding the value which is called the anaerobic threshold (AT), gently increased (FIG. 3). The relationship between the anaerobic threshold (AT) and an approximate value of the heart rate (HR) is expressed by the following expression:

$$HR = \{(220 - Age) - \text{Resting Heart Rate}\} \times 50\% + \text{Resting Heart Rate}.$$

When referring to the graph of FIG. 3, the subject or the like can visually know how the stroke volume (SV) is changed during one exercise (long-distance running for one hour). Specifically, the subject can visually know when the value of the stroke volume (SV) reaches the anaerobic threshold (AT), the degree of increase of the stroke volume (SV) from the quiet time (starting time), and the like.

Figure 4:
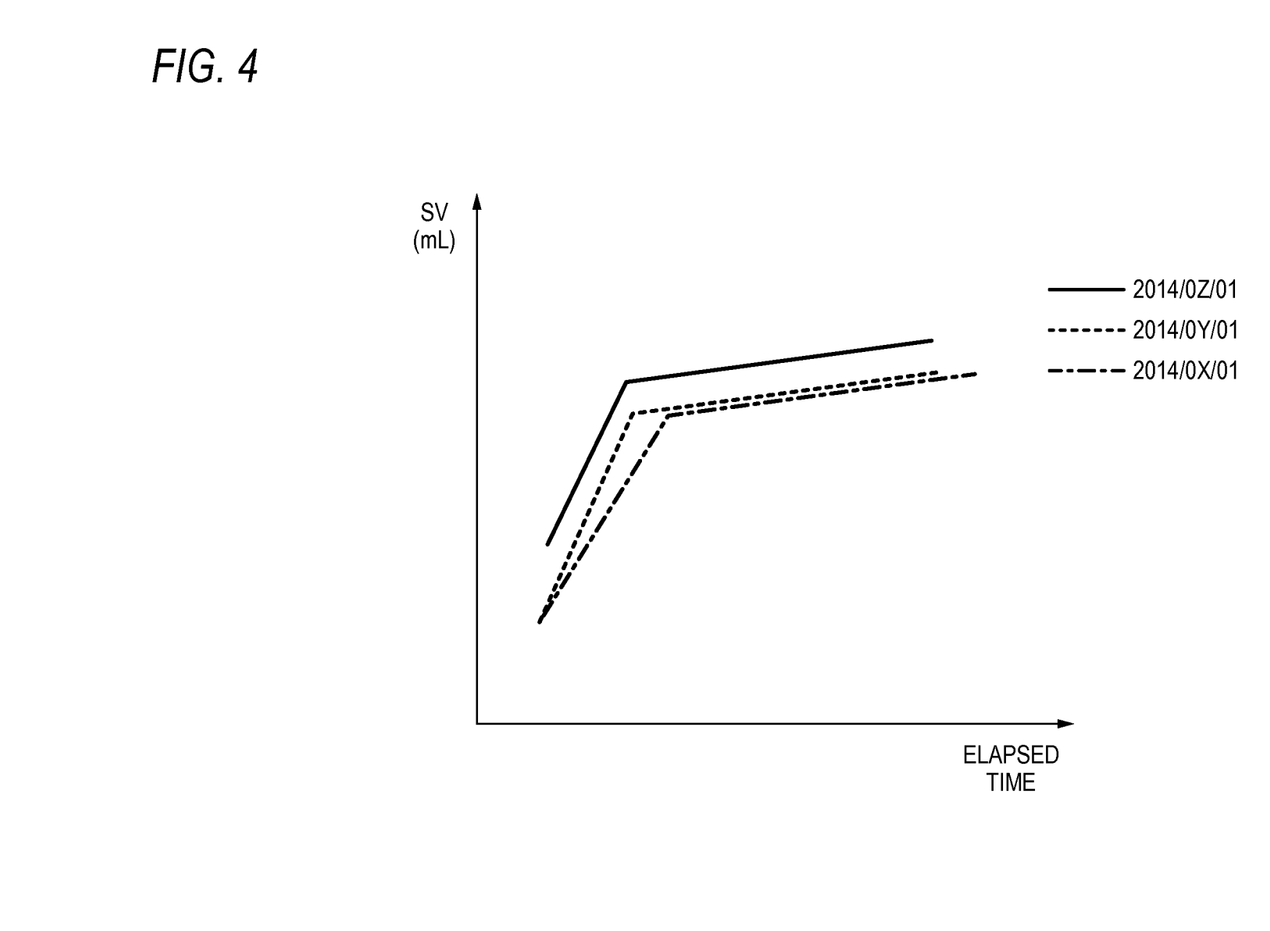
FIG. 4 is a conceptual view showing a third output example of the outputting unit 7 in Embodiment 1.

The outputting unit 7 may display a plurality of temporal changes of the stroke volume (SV) in one exercise such as shown in FIG. 3. FIG. 4 shows an example of this case. The SV calculating unit 6 causes the value of the stroke volume (SV) which is obtained in each day, to be stored in the storage unit 8. Namely, the SV calculating unit 6 acquires a plurality of temporal changes of the stroke volume (SV) in one exercise, and causes the changes to be stored in the storage unit 8.

As shown in FIG. 4, the outputting unit 7 may superimposedly display a plurality of graphs each showing the temporal change of the stroke volume (SV). Preferably, the outputting unit 7 may display also the dates on which the exercises are conducted, as shown in FIG. 4.

When referring to the graph of FIG. 4, the subject can know the degree of change of the stroke volume (SV). For example, the subject can visually know from the graph how the changing tendency of the stroke volume (SV) in one exercise is varied in accordance with progress of training. When the value of the anaerobic threshold (AT) is increased, for example, it is possible to determine that the ability of the stroke volume (SV) is enhanced.

Although, in the examples shown in FIGS. 2 to 4, the outputting unit 7 outputs the stroke volume (SV) calculated by the SV calculating unit 6, in the form of a graph, the output manner is not limited to this. For example, the stroke volume (SV) may be output in the form of a table, and displayed to the subject or the like. The outputting unit 7 is not always necessary to perform a GUI (Graphical User Interface)-based output, and may perform a CUI (Character User Interface)-based output. For example, the outputting unit 7 may output the temporal change of the stroke volume (SV) to a CSV (Comma-Separated Values) file. Moreover, the outputting unit 7 is not always necessary to perform the output so as to clarify the relationship between the stroke volume (SV) and the elapsed time, and may output the stroke volume (SV) as it is at a certain timing to a file or the like.

Then, the effect of the cardiopulmonary function evaluating apparatus 1 of the embodiment will be further described. In the related-art evaluation of the cardiopulmonary function based on the cardiac output (CO), it is impossible to correctly know whether the cardiac output (CO) is increased by increase of the heart rate (HR) or by that of the stroke volume (SV), and therefore the cardiopulmonary function of the subject cannot be correctly evaluated.

In the above-described configuration, by contrast, the SV calculating unit 6 calculates the stroke volume (SV) of the subject. The outputting unit 7 outputs information from which the condition of the stroke volume (SV) of the subject can be known, based on the stroke volume (SV) calculated by the SV calculating unit 6. When referring to the output, it is possible to correctly know the condition of the stroke volume (SV) of the subject. Consequently, the state of the cardiopulmonary function of the subject can be known.

In the case where the outputting unit 7 outputs the temporal change of the stroke volume (SV) as described above, the subject or the like can know the relationship between the elapsed time and the effect of the training. When the output is performed in the form of a graph such as shown in FIGS. 2 to 4, particularly, it is possible to visually know how the stroke volume (SV) of the subject is changed in accordance with progress of training or the like.

Embodiment 2

The cardiopulmonary function evaluating apparatus 1 of Embodiment 2 is mainly characterized in that an evaluation value from which the state of the cardiopulmonary function can be known is calculated based on the stroke volume (SV) calculated by the SV calculating unit 6. Hereinafter, points which are different from Embodiment 1 will be described.

Figure 5:
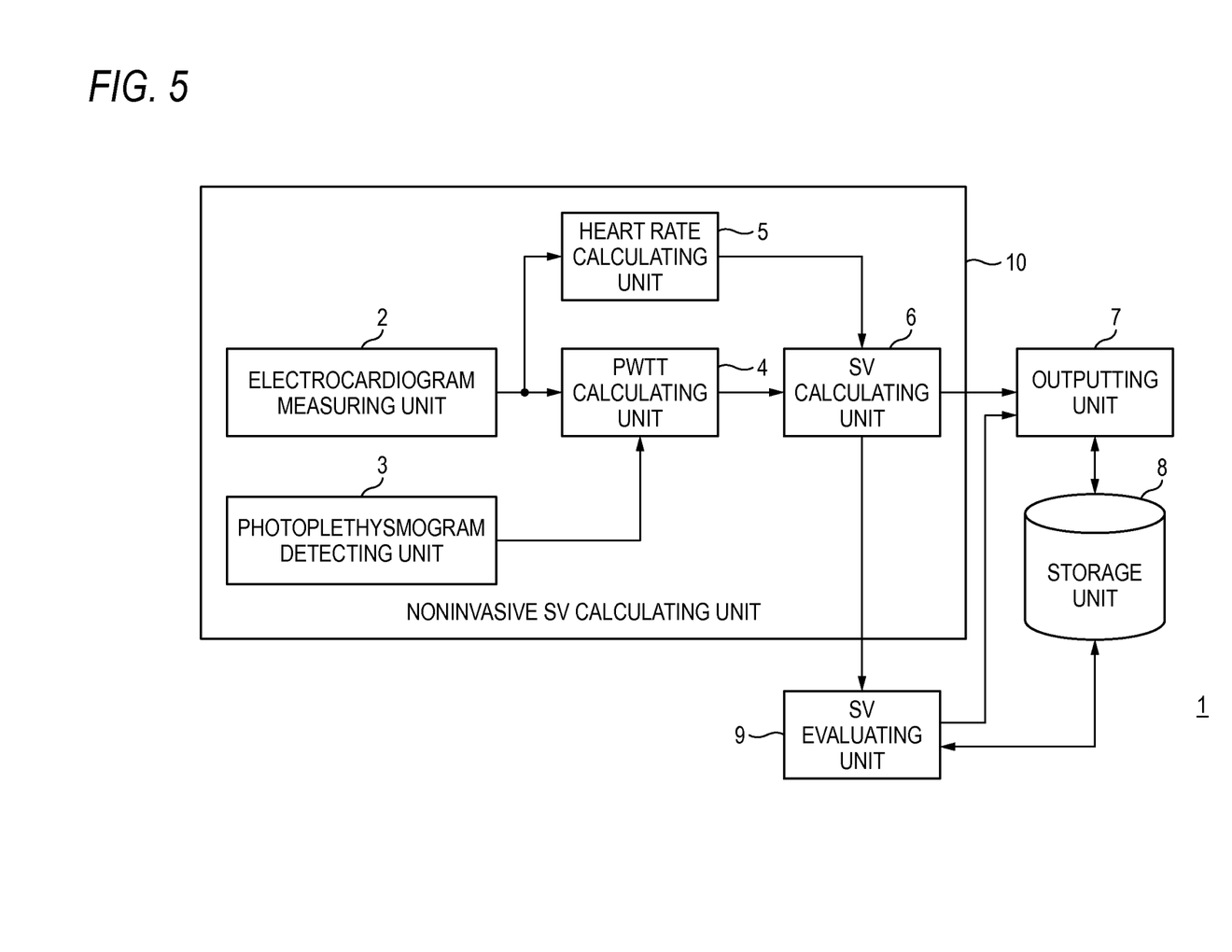
FIG. 5 is a block diagram showing the configuration of a cardiopulmonary function evaluating apparatus 1 of Embodiment 2.

FIG. 5 is a block diagram showing the configuration of a cardiopulmonary function evaluating apparatus 1 of the embodiment. The apparatus further includes an SV evaluating unit 9 in addition of the configuration shown in FIG. 1. The SV calculating unit 6 supplies the value of the calculated stroke volume (SV) to the outputting unit 7 and the SV evaluating unit 9.

The SV evaluating unit 9 compares and evaluates the value of the stroke volume (SV) and an index value related to the stroke volume (SV), and supplies an evaluation value which is obtained in the evaluation, to the outputting unit 7. The evaluation value contains not only a numerical value but also a truth value or the like indicating which one of the index value and the stroke volume (SV) is larger than the other. The index value which is used in the comparison includes values (history values) of stroke volumes (SV) that were calculated by the SV calculating unit 6, a statistical value (for example, an average SV value of the same sex and age as the subject), and the like. Hereinafter, Specific Example 1 of the evaluation performed by the SV evaluating unit 9 will be described with reference to FIG. 6.

Figure 6:
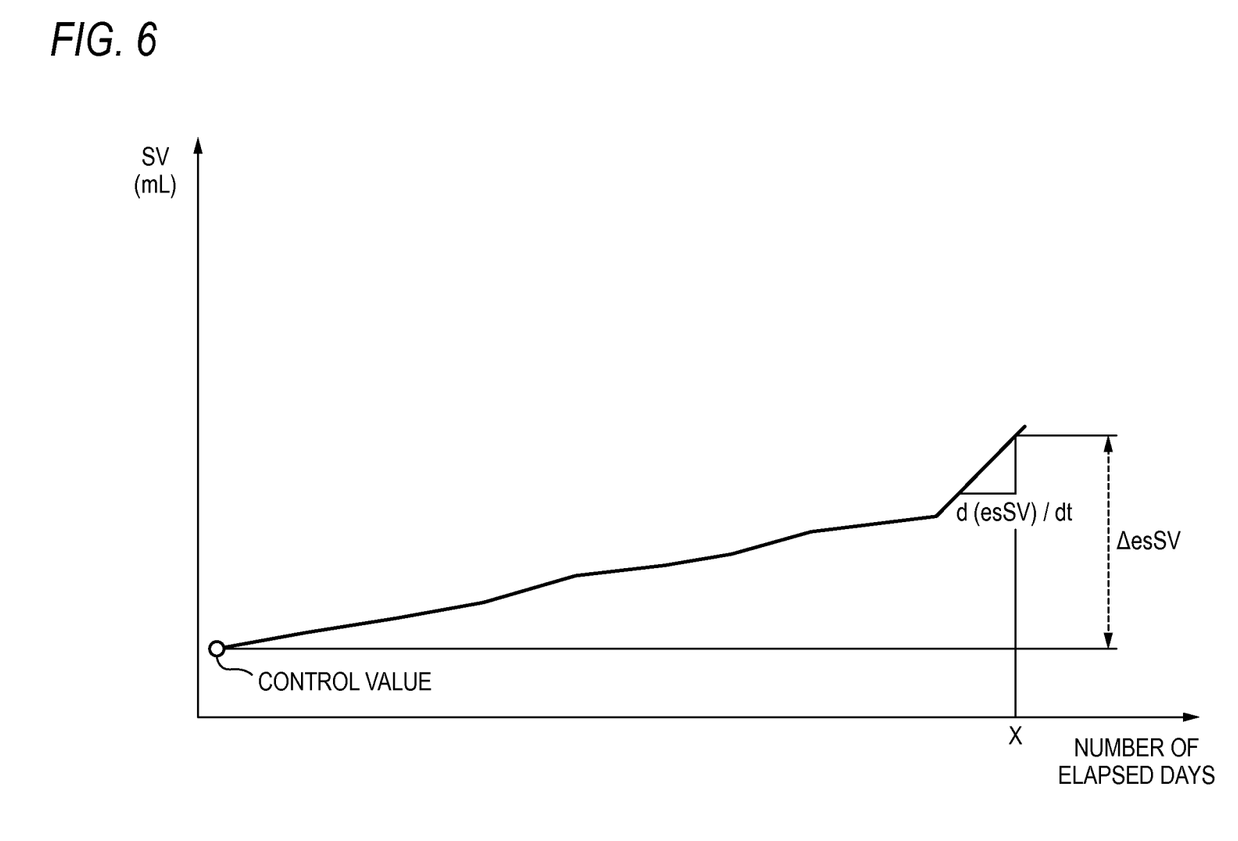
FIG. 6 is a conceptual view showing an evaluation by an SV evaluating unit 9 in Embodiment 2.

As Specific Example 1, an example will be described in which the SV evaluating unit 9 calculates the difference ($\Delta esSV$) between the current stroke volume (SV) calculated by the SV calculating unit 6, and a history value of the stroke volume (SV) which is acquired at a predetermined timing. The subject (or another user) designates a reference timing through an inputting unit (for example, a mouse or keyboard connected to the cardiopulmonary function evaluating apparatus 1). Hereinafter, the value of the stroke volume (SV) at the reference timing is referred to as the control value. The storage unit 8 stores the control value, and the SV evaluating unit 9 adequately reads the control value from the storage unit 8. The SV evaluating unit 9 calculates the difference ($\Delta esSV$) between the current stroke volume (SV) and the control value by a subtraction process, and supplies the difference value ($\Delta esSV$) to the outputting unit 7.

As Specific Example 2, an example will be described in which the SV evaluating unit 9 calculates the amount of change of the current stroke volume (SV) calculated by the SV calculating unit 6. The storage unit 8 holds history values of the stroke volume (SV) such as shown in FIG. 6. The SV evaluating unit 9 calculates the amount of change ($d(esSV)/dt$) of the stroke volume (SV) by using the history values and the current stroke volume (SV) calculated by the SV calculating unit 6. In the calculation process, the amount may be calculated by a usual differential calculation process. The SV evaluating unit 9 supplies the calculated amount of change ($d(esSV)/dt$) of the stroke volume (SV) to the outputting unit 7.

Figure 7:
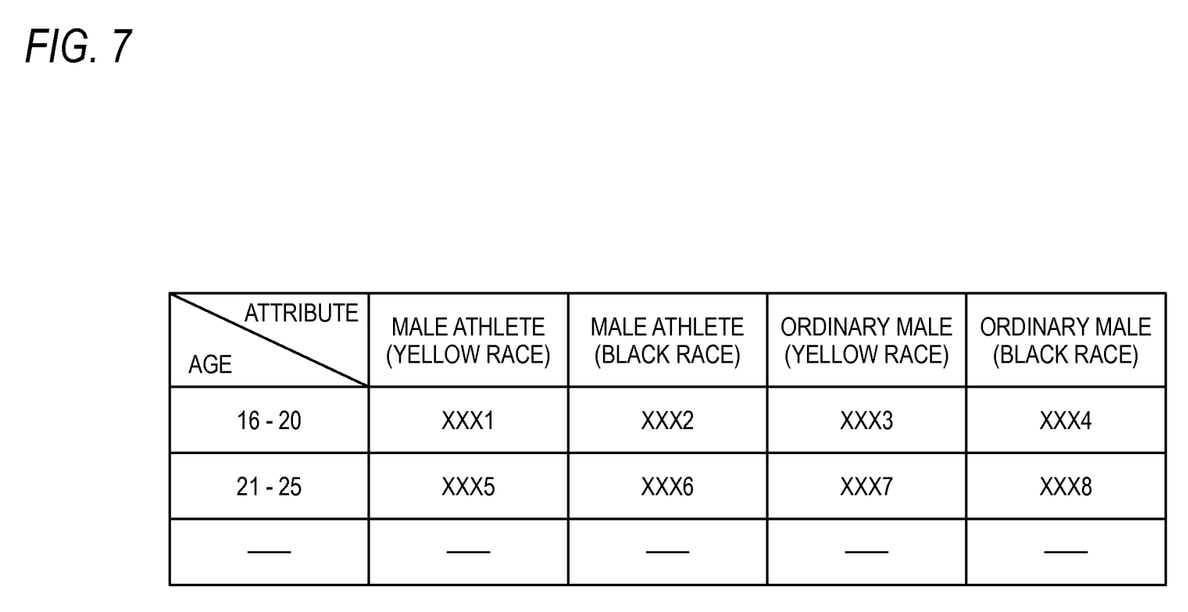
FIG. 7 is a table showing a specific example of statistical values which are used in a comparison evaluation by the SV evaluating unit 9 in Embodiment 2.

The evaluation process of the SV evaluating unit 9 is not limited to the comparison with the stroke volume (SV) which has been acquired. As Specific Example 3, a process of comparing the current stroke volume (SV) with a statistical value will be described. FIG. 7 is a table showing a specific example of statistical values. The table shows relationship between the attribute (a male athlete (yellow race) and the like) and the age, and the average value of the stroke volume (SV). Here, the average value of the stroke volume (SV) may be that of stroke volumes (SV) which are measured at a predetermined timing in one exercise (for example, after elapse of 45 minutes from the start of long-distance running for one hour). In the example of FIG. 7, the average value of the stroke volumes (SV) of 16- to 20-year-old male athletes (yellow race) is "XXX1".

The SV evaluating unit 9 compares the stroke volume (SV) calculated by the SV calculating unit 6, with corresponding data in the table, to evaluate whether the stroke volume (SV) of the subject is larger than the average or not. The SV evaluating unit 9 may calculate a truth value indicating whether the volume is larger than the average value or not, or the difference value between the volume and the average value. The SV evaluating unit 9 supplies the calculated value (the truth value or the difference value) to the outputting unit 7.

Although the specific examples of the evaluation by the SV evaluating unit 9 have been described, another evaluation may be performed. The stroke volume (SV) calculated by the SV calculating unit 6, and the various evaluation values ($\Delta esSV$, $d(esSV)/dt$, and the like) which are calculated in the evaluation process by the SV evaluating unit 9 are input to the outputting unit 7. The outputting unit 7 outputs a part or all of the inputs.

Figure 8:
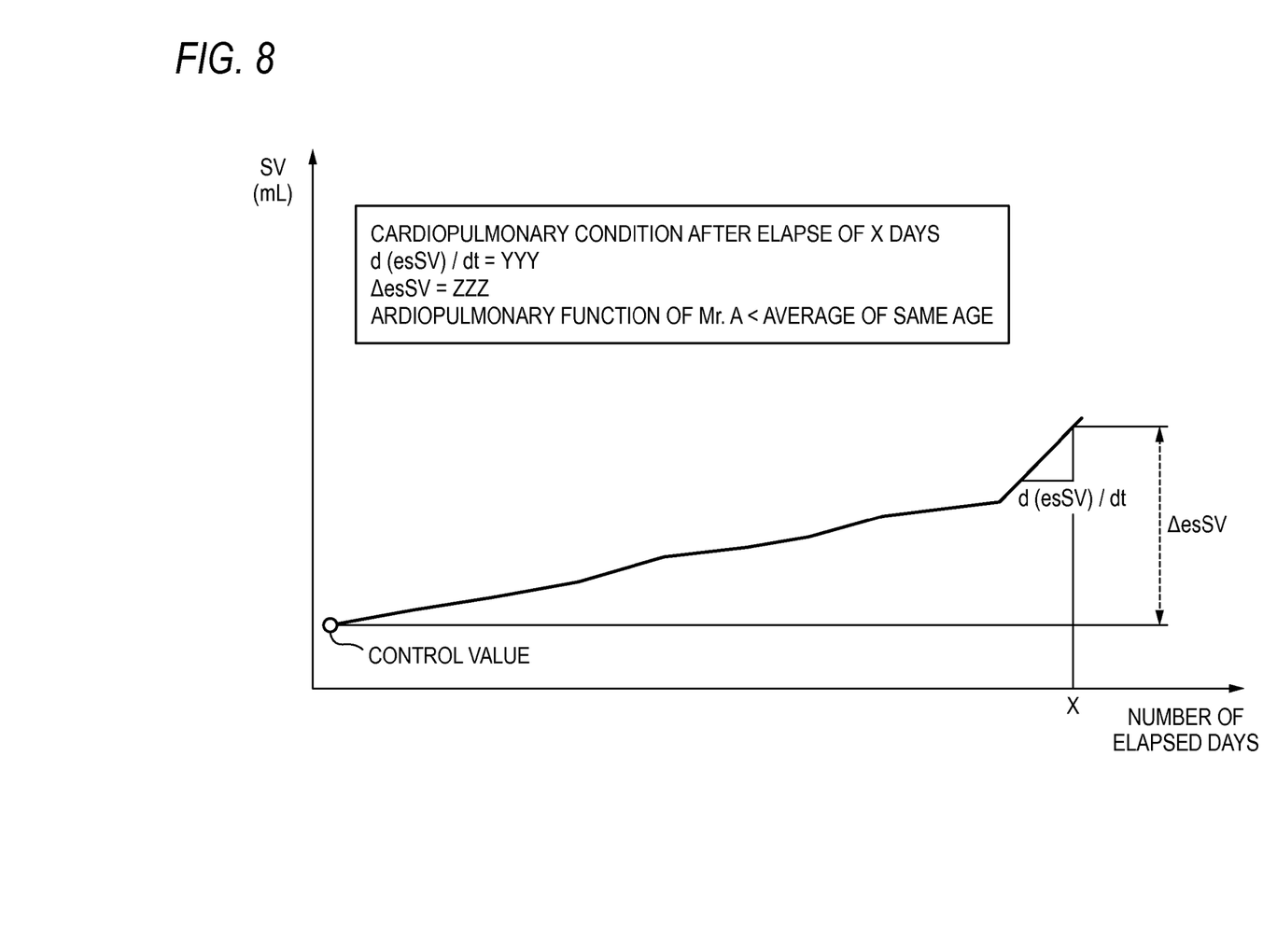
FIG. 8 is a conceptual view showing a first output example of an outputting unit 7 in Embodiment 2.

For example, the outputting unit 7 may write the various evaluation values ($\Delta esSV$, $d(esSV)/dt$, and the like) as an electronic file in the storage unit 8. Moreover, the outputting unit 7 may display the evaluation values together with the temporal change of the stroke volume (SV). FIG. 8 shows a display example.

In FIG. 8, the change of the stroke volume (SV) with respect to the elapsed days, and the present (at the timing when X days have elapsed) evaluation values (ΔesSV, d(esSV)/dt, and the like) are superimposedly displayed. The display shown in FIG. 8 is a mere example, and a display screen other than this may be used. When referring to the screen shown in FIG. 8, the subject can visually know the condition of the stroke volume (SV), and also correct numerical values related to the stroke volume (SV).

Effects of the cardiopulmonary function evaluating apparatus 1 of the embodiment will be described. As described above, the SV evaluating unit 9 calculates the various evaluation values (ΔesSV, d(esSV)/dt, and the like) indicating the condition of the stroke volume (SV) of the subject. When referring to these evaluation values, the subject or the like can correctly know the condition of the stroke volume (SV) of the subject, and consequently the state of the cardiopulmonary function of the subject.

In the case where the SV evaluating unit 9 calculates ΔesSV, for example, the subject or the like can correctly know the degree of change (the rising or lowering degree) of the stroke volume (SV) from a specific timing (for example, a state where no training is performed), as a numerical value.

In the case where the SV evaluating unit 9 calculates (d(esSV)/dt), the subject or the like can correctly know the training strength (or the rate of the improvement effect of the cardiopulmonary function) at the timing when the amount of change (d(esSV)/dt) is calculated.

In the case where the SV evaluating unit 9 compares a statistical value (for example, an average value of the same sex and age) with the stroke volume (SV) of the subject, the subject or the like can correctly know the ability degree of the subject in the same category.

Although the invention conducted by the inventor has been specifically described based on the exemplary embodiments, the invention is not limited to the above-described embodiments, and it is a matter of course that various changes can be made without departing from the spirit of the invention.

Although the examples in which the subject performs long-distance running have been mainly described, it is a matter of course that above-described the cardiopulmonary function evaluating apparatus 1 can be used also in light-load exercise (for example, rehabilitation). The cardiopulmonary function evaluating apparatus 1 is not limited to an apparatus of the type in which the apparatus is attached to the subject, and may be an apparatus which is to be used at bedside.

According to the presently disclosed subject matter, there is provided a cardiopulmonary function evaluating apparatus comprising: an electrocardiogram measuring unit which is configured to measure an electrocardiogram of a subject; a photoplethysmogram detecting unit which is configured to detect a photoplethysmogram of the subject; a heart rate calculating unit which is configured to calculate a heart rate (HR) of the subject based on the electrocardiogram; a PWTT calculating unit which is configured to calculate a pulse wave transmission time (PWTT) of the subject based on the electrocardiogram and the photoplethysmogram; an SV calculating unit which is configured to calculate a stroke volume (SV) of the subject based on the heart rate (HR) and the pulse wave transmission time (PWTT); and an outputting unit which is configured to output a state related to the stroke volume (SV) of the subject based on the stroke volume (SV) that is calculated by the SV calculating unit.

In the above configuration, the SV calculating unit calculates the stroke volume (SV) of the subject, and the outputting unit outputs information from which the stroke volume (SV) of the subject can be known, based on the stroke volume (SV) calculated by the SV calculating unit. When referring to the output, it is possible to correctly know the state of the stroke volume (SV) of the subject. Consequently, the state of the cardiopulmonary function of the subject can be known.

The outputting unit may output a temporal change of the stroke volume (SV) that is calculated by the SV calculating unit.

When referring to the output temporal change of the stroke volume (SV), it is possible to correctly know the relationship between the temporal change and the stroke volume (SV).

The outputting unit may output the temporal change of the stroke volume (SV) that is calculated by the SV calculating unit, in a form of a graph.

When visually referring to the temporal change of the stroke volume (SV), it is possible to correctly and intuitively know the relationship between the temporal change and the stroke volume (SV).

The outputting unit may display a temporal change of the stroke volume (SV) which is acquired by the SV calculating unit in one exercise, on the graph.

In the configuration where the temporal change of the stroke volume (SV) is displayed in the form of a graph, it is possible to visually know how the stroke volume (SV) of the subject is changed during one exercise (for example, from the beginning of long-distance running in a certain day to the end of the running).

The SV calculating unit may acquire a plurality of temporal changes of the stroke volume (SV) in one exercise, and the outputting unit may superimposedly display a plurality of graphs based on the plurality of temporal changes of the stroke volumes (SV) which are acquired by the SV calculating unit.

In the configuration where graphs are superimposedly displayed, it is possible to simultaneously know changes of the stroke volume (SV) in exercises.

The cardiopulmonary function evaluating apparatus may further comprise: an SV evaluating unit which is configured to evaluate a cardiopulmonary ability of the subject, based on the stroke volume (SV) calculated by the SV calculating unit and an index value related to the stroke volume (SV), and the outputting unit may output a result of the evaluation by the SV evaluating unit, as the state related to the stroke volume (SV) of the subject.

When referring to the evaluation values, the subject or the like can correctly know the state of the stroke volume (SV) of the subject, and consequently the state of the cardiopulmonary function of the subject.

The index value may include at least one of a history value of a stroke volume (SV) calculated by the SV calculating unit, and a statistical value of stroke volumes (SV) related to the subject.

The SV evaluating unit may calculate a difference (ΔesSV) between a current stroke volume (SV) which is calculated by the SV calculating unit, and the history value which is acquired at a predetermined timing.

When referring to ΔesSV, the subject (or another user) can correctly know the degree of change (the rising or lowering degree) of the stroke volume (SV) from a certain timing (for example, a state where no training is performed), as a numerical value.

The SV evaluating unit may refer to the history value, and calculate an amount of change (d(esSV)/dt) of the current stroke volume (SV) calculated by the SV calculating unit.

When referring to the amount of change (d(esSV)/dt), the subject (or another user) can correctly know the training strength (or the rate of the improvement effect of the cardiopulmonary function) at the timing when the amount of change (d(esSV)/dt) is calculated.

The SV evaluating unit may compare and evaluate the statistical value and the current stroke volume (SV) calculated by the SV calculating unit.

When the comparison is performed, it is possible to correctly know, for example, whether the stroke volume (SV) of the subject is larger than the average value or not.

There is also provided a cardiopulmonary function evaluating apparatus comprising: a noninvasive SV calculating unit which is configured to calculate a stroke volume (SV) of a subject by using a noninvasive technique; and an outputting unit which is configured to output a state related to the stroke volume (SV) of the subject based on the stroke volume (SV) that is calculated by the noninvasive SV calculating unit.

In the above configuration, the noninvasive SV calculating unit calculates the stroke volume (SV) of the subject by using the noninvasive technique, and the outputting unit outputs information from which the stroke volume (SV) of the subject can be known, based on the stroke volume (SV) calculated by the SV calculating unit. When referring to the output, it is possible to correctly know the state of the stroke volume (SV) of the subject. Consequently, the state of the cardiopulmonary function of the subject can be known.

The presently disclosed subject matter can provide a cardiopulmonary function evaluating apparatus and cardiopulmonary function evaluating method in which the state of the cardiopulmonary function (for example, the degree of improvement in cardiopulmonary function, and comparisons with cardiopulmonary functions of the same generation) of the subject can be adequately known by using the stroke volume (SV).

What is claimed is:

1. A cardiopulmonary function evaluating apparatus comprising:
   an electrocardiogram measuring unit which is configured to measure an electrocardiogram of a subject based on signals from at least one electrocardiogram electrode;
   a photoplethysmogram detecting unit which is configured to detect a photoplethysmogram of the subject; and
   at least one processor configured to:
      calculate a heart rate (HR) of the subject based on the electrocardiogram;
      calculate a pulse wave transmission time (PWTT) of the subject based on the electrocardiogram and the photoplethysmogram;
      calculate a stroke volume (SV) of the subject based on the heart rate (HR) and the pulse wave transmission time (PWTT);
      output a state related to the stroke volume (SV) of the subject based on the calculated stroke volume (SV);
      acquire a temporal change of the stroke volume (SV) in one exercise a plurality of times; and
      superimposedly display a plurality of the temporal change of the stroke volume (SV) in the one exercise.

2. The cardiopulmonary function evaluating apparatus according to claim 1, wherein the processor is further configured to
   evaluate a cardiopulmonary ability of the subject, based on the calculated stroke volume (SV) and an index value related to the stroke volume (SV); and
   output a result of the evaluation of the cardiopulmonary ability as the state related to the stroke volume (SV) of the subject.

3. The cardiopulmonary function evaluating apparatus according to claim 1, wherein the index value includes at least one of a history value of the calculated stroke volume (SV), and a statistical value of stroke volumes (SV) related to the subject.

4. The cardiopulmonary function evaluating apparatus according to claim 3, wherein the processor is further configured to calculate a difference ($\Delta$esSV) between the current stroke volume (SV) and the history value which is acquired at a predetermined timing.

5. The cardiopulmonary function evaluating apparatus according to claim 3, wherein the processor is further configured to:
   refer to the history value, and
   calculate an amount of change (d(esSV)/dt) of the current stroke volume (SV).

6. The cardiopulmonary function evaluating apparatus according to claim 3, wherein the processor is further configured to compare and evaluate the statistical value and the current stroke volume (SV).

7. A cardiopulmonary function evaluating method comprising:
   measuring an electrocardiogram of a subject;
   detecting a photoplethysmogram of the subject;
   calculating a heart rate (HR) of the subject based on the electrocardiogram;
   calculating a pulse wave transmission time (PWTT) of the subject based on the electrocardiogram and the photoplethysmogram;
   calculating a stroke volume (SV) of the subject based on the heart rate (HR) and the pulse wave transmission time (PWTT); and
   outputting a state related to the stroke volume (SV) of the subject based on the calculated stroke volume (SV);
   acquiring a temporal change of the stroke volume (SV) in one exercise a plurality of times; and
   superimposedly displaying a plurality of the temporal change of the stroke volume (SV) in the one exercise.

8. The cardiopulmonary function evaluating method according to claim 7, further comprising:
   evaluating a cardiopulmonary ability of the subject, based on the calculated stroke volume (SV) and an index value related to the stroke volume (SV), and
   outputting a result of the evaluation of the cardiopulmonary ability as the state related to the stroke volume (SV) of the subject.

9. The cardiopulmonary function evaluating method according to claim 8, wherein the index value includes at least one of a history value of the calculated stroke volume (SV), and a statistical value of stroke volumes (SV) related to the subject.

10. The cardiopulmonary function evaluating method according to claim 9, further comprising calculating a difference ($\Delta$esSV) between the current stroke volume (SV) and the history value which is acquired at a predetermined timing.

11. The cardiopulmonary function evaluating method according to claim 9, further comprising calculating an amount of change (d(esSV)/dt) of the current stroke volume (SV).

12. The cardiopulmonary function evaluating method according to claim 9, further comprising comparing and evaluating the statistical value and the current stroke volume (SV).

\* \* \* \* \*